(12) United States Patent
Elenbaas et al.

(10) Patent No.: US 10,535,149 B2
(45) Date of Patent: Jan. 14, 2020

(54) IMAGING DEVICE FOR REGISTRATION OF DIFFERENT IMAGING MODALITIES

(71) Applicant: KONINKLIJKE PHILIPS N.V., Eindhoven (NL)

(72) Inventors: Thijs Elenbaas, Eindhoven (NL); Javier Olivan Bescos, Eindhoven (NL); Eberhard Sebastian Hansis, Hamburg (DE); Kirsten Helena Zuurmond, Eindhoven (NL)

(73) Assignee: KONINKLIJKE PHILIPS N.V., Eindhoven (NL)

( * ) Notice: Subject to any disclaimer, the term of this patent is extended or adjusted under 35 U.S.C. 154(b) by 96 days.

(21) Appl. No.: 15/319,207

(22) PCT Filed: Jun. 25, 2015

(86) PCT No.: PCT/EP2015/064401
§ 371 (c)(1),
(2) Date: Dec. 15, 2016

(87) PCT Pub. No.: WO2015/197770
PCT Pub. Date: Dec. 30, 2015

(65) Prior Publication Data
US 2017/0148180 A1    May 25, 2017

(30) Foreign Application Priority Data
Jun. 25, 2014 (EP) .................................... 14173817

(51) Int. Cl.
*G06K 9/00* (2006.01)
*G06T 7/38* (2017.01)
(Continued)

(52) U.S. Cl.
CPC ................ *G06T 7/38* (2017.01); *A61B 5/055* (2013.01); *A61B 6/032* (2013.01); *G06T 7/0012* (2013.01);
(Continued)

(58) Field of Classification Search
None
See application file for complete search history.

(56) References Cited

U.S. PATENT DOCUMENTS

| 6,370,417 B1 | 4/2002 | Bani-Hashemi |
| 2010/0246915 A1 | 9/2010 | Goshin |

(Continued)

FOREIGN PATENT DOCUMENTS

| JP | 2013123227 A | 6/2013 |
| WO | 2006051488 A1 | 5/2006 |

(Continued)

OTHER PUBLICATIONS

Tang, Lisa et al "Co-registration of Bone CT and SPECT Images Using Mutual Information", 2006 IEEE International Symposium on Signal Processing and Information Technology.

*Primary Examiner* — Wei Wen Yang (57) ABSTRACT

The invention relates to an imaging device (10) for registration of different imaging modalities, an imaging system (1) for registration of different imaging modalities, a method for registration of different imaging modalities, a computer program element for controlling such device and a computer readable medium having stored such computer program element. The imaging system (1) for registration of different imaging modalities comprises a first imaging modality (2), a second imaging modality (3), and an imaging device (10) for registration of different imaging modalities. The imaging device (10) for registration of different imaging modalities comprises a model provision unit (11), a first image data provision unit (12), a processing unit (13), a second image (Continued)

data provision unit (14), and a registration unit (15). The model provision unit (11) provides a cavity model of a visceral cavity. The first image data provision unit (12) provides first image data showing a region of interest of a patient by the first imaging modality (2). The processing unit (13) registers the cavity model to the first image data and adapts the cavity model based on the first image data. The processing unit (13) differs between bony and non-bony structures and masks a non-bony structure in the first image data based on the adapted cavity model. The second image data provision unit (14) provides second image data showing the region of interest of a patient by the second imaging modality (3). The registration unit (15) registers the masked first image data and the second image data.

20 Claims, 4 Drawing Sheets

(51) Int. Cl.
  *G06T 7/149* (2017.01)
  *G06T 7/11* (2017.01)
  *A61B 5/055* (2006.01)
  *A61B 6/03* (2006.01)
  *G06T 7/00* (2017.01)
  *H04N 7/18* (2006.01)

(52) U.S. Cl.
  CPC ............... *G06T 7/11* (2017.01); *G06T 7/149* (2017.01); *H04N 7/181* (2013.01); *G06T 2207/10016* (2013.01); *G06T 2207/10081* (2013.01); *G06T 2207/10088* (2013.01); *G06T 2207/10116* (2013.01); *G06T 2207/30008* (2013.01)

(56) References Cited

U.S. PATENT DOCUMENTS

| | | |
|---|---|---|
| 2011/0182492 A1 | 7/2011 | Grass |
| 2013/0064438 A1* | 3/2013 | Taylor ................ A61B 5/02007 382/130 |
| 2013/0182925 A1 | 7/2013 | Razeto |
| 2013/0314440 A1* | 11/2013 | Simon ................... G06T 7/0014 345/629 |
| 2014/0126789 A1 | 5/2014 | Ban |
| 2014/0133727 A1* | 5/2014 | Oktay ....................... G06T 7/33 382/131 |
| 2014/0313196 A1* | 10/2014 | Mistretta ............... G06T 11/008 345/424 |
| 2014/0369584 A1* | 12/2014 | Fan ......................... A61B 6/501 382/131 |
| 2015/0313566 A1 | 11/2015 | Diers |
| 2016/0235482 A1* | 8/2016 | Wood ..................... A61B 1/043 |

FOREIGN PATENT DOCUMENTS

| | | |
|---|---|---|
| WO | 2006063141 A2 | 6/2006 |
| WO | 2007057845 A1 | 5/2007 |
| WO | 2013132402 A2 | 9/2013 |
| WO | 2014031531 A1 | 2/2014 |
| WO | 2014033584 A1 | 3/2014 |

* cited by examiner

IMAGING DEVICE FOR REGISTRATION OF DIFFERENT IMAGING MODALITIES

CROSS-REFERENCE TO PRIOR APPLICATIONS

This application is the U.S. National Phase application under 35 U.S.C. § 371 of International Application No. PCT/EP2015/064401, filed on Jun. 25, 2015, which claims the benefit of European Patent Application No. 14173817.9, filed on Jun. 25, 2014. These applications are hereby incorporated by reference herein.

FIELD OF THE INVENTION

The invention relates to an imaging device for registration of different imaging modalities, an imaging system for registration of different imaging modalities, a method for registration of different imaging modalities, a computer program element for controlling such device and a computer readable medium having stored such computer program element.

BACKGROUND OF THE INVENTION

During a procedure that uses multiple imaging modalities, for example CT and live X-ray, a physician will need to register the modalities. In common applications that use manual 2D-3D registration, this is done in the following manner: The physician moves a C-arm to a certain angulation that gives him a clear view on landmarks in the body that can be used for registration, for example the pelvic bone. He will then acquire an exposure run or a single shot image. Next, the physician will move the C-arm to a different angulation that is sufficiently different (more than 45 degrees difference) and shoot another exposure or single shot.

Both X-ray runs are shown in different viewports of the application, where they are blended with appropriately rotated volume views of the CT volume. The physician will now move the CT in both views such that it optimally overlaps the live X-ray. The visual markers that the physician uses to determine optimal overlap are usually bony landmarks, such as the pelvis, spine or ribcage.

WO 2013/132402 A2 discloses hereto a system for image registration. It includes an image feature detection module configured to identify internal landmarks of a first image. An image registration and transformation module is configured to compute a registration transformation, to register a second image with the first image based on surface landmarks to result in a registered image. A landmark identification module is configured to overlay the internal landmarks onto the second image using the registration transformation, encompass each of the overlaid landmarks within a virtual object to identify corresponding landmark pairs in the registered image, and register the second image with the first image using the registered image with the identified landmarks.

SUMMARY OF THE INVENTION

Hence, there may be a need to provide an imaging device for registration of different imaging modalities, which improves a registration of image data of the visceral cavity taken by multiple different imaging modalities.

The problem of the present invention is solved by the subject-matters of the independent claims, wherein further embodiments are incorporated in the dependent claims. It should be noted that the aspects of the invention described in the following apply also to the imaging device for registration of different imaging modalities, the imaging system for registration of different imaging modalities, the method for registration of different imaging modalities, the computer program element, and the computer readable medium.

According to the present invention, an imaging device for registration of different imaging modalities is presented. The imaging device for registration of different imaging modalities comprises a model provision unit, a first image data provision unit, a processing unit, a second image data provision unit, and a registration unit. In the following a short overview of these components is given, followed by a more detailed description below.

The model provision unit is configured to provide a cavity model of a ventral cavity. That is, a deformable model of the ventral cavity (hereinafter also referred to as "visceral cavity") may be provided that incorporates model representations of, for example, organs in the thoracic, abdominal and pelvic cavities. Thus, the model preferably includes at least one organ of the chest and/or abdomen, such as the lungs or kidneys.

Such a deformable model may initially be generated from one or several training image datasets in which the features of interest are segmented or annotated manually. Landmark detection for model localization, edge feature detection, and typical shape variations can likewise be learned from training data.

The first image data provision unit is configured to provide first image data showing a region of interest of a patient by a first modality. In an example, the first image data of the first modality are CT or MR image data.

The processing unit is configured to register the cavity model to the first image data and to adapt the cavity model based on the first image data. Thereby, an adapted cavity model is achieved. The adaptation may for example be achieved through minimizing, based on the image data, energy parameters associated with the deformable model, so that features represented in the model, such as organs, are adapted to corresponding features in the image data in an optimal manner.

The processing unit is configured to mask at least a part of the ventral cavity in the first image data based on the adapted cavity model. Thereby, masked first image data are achieved.

The second image data provision unit is configured to provide second image data showing at least part of the region of interest of a patient by a second modality. In an example, the second image data of the second modality are live X-ray image data.

The registration unit is configured to register the masked first image data and the second image data. In an example, an overlay of CT or MR image data on live X-ray data is achieved.

In other words, the present invention relates to an imaging device for registration of different imaging modalities for optimal registration in the thoracic and/or abdominal area.

While pelvic bones are relatively easy to distinguish in the live X-ray and the 3D volume, this is more difficult for the spine and ribcage. This is, among other factors, due to the tissue and the often contrast enhanced vasculature inside the visceral cavity cluttering the view on these structures in the CT.

The imaging device according to the present invention advantageously allows obtaining a clearer view on such bony structures. In particular, the visibility of the spine and the ribcage may be enhanced by virtue of the masking of structures inside the visceral cavity, in particular a (contrast enhanced) vascular structure.

A registration between different image data sets usually is based on landmarks; in case of registering a CT or MR data set and live X-ray data, the registration usually involves bony landmarks, such as the pelvis, spine or ribcage.

In accordance with the invention, the total amount of information in the first image data is reduced by virtue of the masking, whereby a user can better distinguish landmarks and in particular overlap of image information corresponding to landmarks between the different imaging modalities, enabling an optimal registration.

Preferably, the imaging device according to the invention allows selectively rendering sub-volumes of bony landmarks. Thus, it is for example possible to enable or disable rendering of the spine, the pelvic bone, or the ribs or the rib cage for optimal registration. The imaging device thus allows a selective visualization of landmark structures during manual or automatic 2D-3D registration, such that the registration consumes minimal time and is as accurate as possible.

In an example, the visceral ventral cavity in the first image data is segmented based on the adaptation of the cavity model. Thus, a model-based segmentation is performed as is generally known in the art.

The segmentation of the visceral cavity may include at least one organ of a chest and/or an abdomen, for which a representation is included in the model. The segmentation may include a model-based segmentation of an outer surface of the visceral cavity, which results in a surface model of the visceral cavity.

The adapting of the cavity model based on the first image data may be performed in a fully automatic fashion.

The registration of the masked first image data and the second image data can be performed manually, in a semi-automatic or a fully automatic fashion. To this end, the alignment of e.g. CT to X-ray may be performed using known 2D-3D registration methods.

The user can be given the option to initialize or post-correct the automatic segmentation. Using bony landmarks as reference for the automatic registration improves the robustness and accuracy of the registration, in particular because the contrast agent filling and detailed geometry of the vasculature may differ between the first, e.g. CT images and the second, e.g. X-ray images.

In an example, the processing unit is configured to mask tissue and/or a vasculature structure in the first image data based on the adapted cavity model. The tissue and/or the vasculature structure may be contrast-enhanced in the first image data. By masking all voxels inside the visceral cavity, (contrast-enhanced) vasculature and other contents of the visceral cavity are removed from the first image data visualization.

In an example, the processing unit is configured to estimate a sub-volume of bony landmarks in the first image data based on at least one parameter of the adapted cavity model. In particular, the volumes of the spine, rib cage, and pelvic bones regions can be estimated from one or more model parameters, such as a volume enclosed by the ventral cavity outer surface. Thus, sub-volume masks for each of these bony landmark structures can be generated accordingly.

In an example, the processing unit is configured to selectively render the bony landmarks in the first image data based on one or more of the corresponding sub-volume masks. By selectively rendering one or several of these sub-volumes, e.g., only the spine, or the spine and the rib cage, can be shown in e.g. the CT volume visualization. This will serve to better show to a user whether an overlap between the bony structures and/or landmarks in a 3D volume and in the second image data as e.g. X-ray image data is optimal and thereby further helps the physician to attain an optimal registration.

According to the present invention, also an imaging system for registration of different imaging modalities is presented. The imaging system for registration of different imaging modalities comprises a first imaging modality, a second imaging modality, and the imaging device for registration of different imaging modalities as described above. The first and second imaging modalities acquire the first and second image data provided by the first and second image data provision units.

In an example, the imaging system for registration of different imaging modalities further comprises a display unit configured to visualize the registered image data and a landmark within the registered image data to allow an inspection of the registration. The landmark may be based on a bony structure.

In an example, the imaging system for registration of different imaging modalities further comprises a selector configured to select between the visualization of the enclosed volume or of a sub-volume. The sub-volume maybe e.g. a spine sub-volume and/or a rib cage sub-volume. By interacting with the selector, the user can choose to visualize the volume as, e.g. a full volume, a spine and rib cage visualization and/or a spine only volume.

In an example, the imaging system for registration of different imaging modalities further comprises an input device configured to control the segmentation and/or an alignment of the registration. The segmentation and/or alignment of the registration may be based on the selected visualization of the enclosed volume or of a sub-volume. By using the input device, the user may align e.g. the CT and X-ray image data sets, using the selective CT visualization as a guideline.

In an example, the imaging system for registration of different imaging modalities further comprises a bone booster unit configured to boost a visualization of a bone and/or a bony landmark in the second image data, and in particular in 2D X-ray image data. Bone boosting makes registration less time consuming and significantly more accurate.

According to the present invention, also a method for registration of different imaging modalities is presented. It comprises the following steps:

providing a cavity model of a visceral cavity,
providing first image data,
adapting the cavity model based on the first image data,
masking non-bony structures in the first image data based on the adapted cavity model, and
registering the masked first image data and the second image data.

The method for registration of different imaging modalities may further comprise a step of generating the cavity model by segmentation of the visceral cavity, preferably by model-based segmentation of a surface of the visceral cavity.

The method for registration of different imaging modalities may further comprise a step of mask tissue and/or a vasculature structure, preferably contrast-enhanced in the first image data based on the adapted cavity model.

The method for registration of different imaging modalities may further comprise a step of estimating an enclosed volume or sub-volume of the bony structure in the first image data based on the geometry of the adapted cavity model.

The method for registration of different imaging modalities may further comprise a step of selectively rendering the enclosed volume or sub-volume in the first image data.

According to the present invention, also a computer program element is presented, wherein the computer program element comprises program code means for causing an imaging device as defined in the independent device claim to carry out the steps of the method for registration as defined in the independent method claim, when the computer program is run on a computer controlling the imaging device.

It shall be understood that the imaging device for registration of different imaging modalities, the imaging system for registration of different imaging modalities, the method for registration of different imaging modalities, the computer program element for controlling such device and the computer readable medium having stored such computer program element according to the independent claims have similar and/or identical preferred embodiments, in particular, as defined in the dependent claims. It shall be understood further that a preferred embodiment of the invention can also be any combination of the dependent claims with the respective independent claim.

These and other aspects of the present invention will become apparent from and be elucidated with reference to the embodiments described hereinafter.

BRIEF DESCRIPTION OF THE DRAWINGS

Exemplary embodiments of the invention will be described in the following with reference to the accompanying drawings.

DETAILED DESCRIPTION OF EMBODIMENTS

Figure 1:
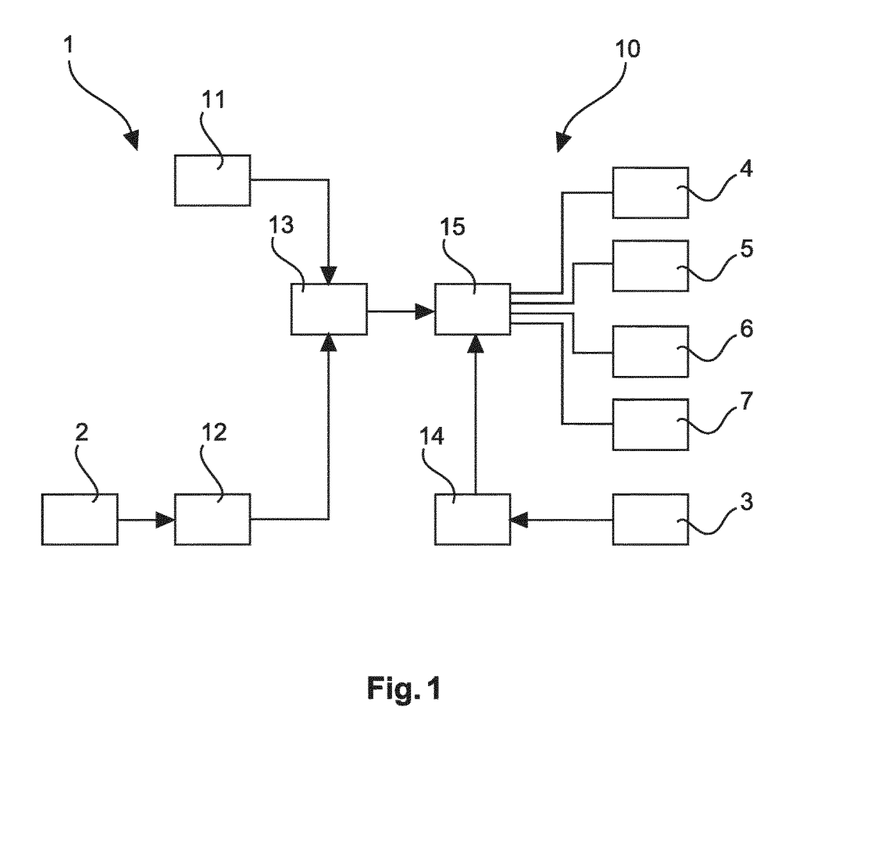
FIG. 1 shows a schematic drawing of an example of an imaging system for registration of different imaging modalities.

FIG. 1 shows schematically and exemplarily an embodiment of an imaging system 1 for registration of different imaging modalities according to the invention. The imaging system 1 for registration of different imaging modalities comprises a first imaging modality 2, a second imaging modality 3, and an imaging device 10 for registration of different imaging modalities.

The imaging device 10 for registration of different imaging modalities comprises a model provision unit 11, a first image data provision unit 12, a processing unit 13, a second image data provision unit 14, and a registration unit 15.

The model provision unit 11 provides a cavity model of a visceral cavity. That is, a deformable model of the visceral cavity may be provided that incorporates model representations of, for example, organs in the thoracic, abdominal and pelvic cavities such as the lungs or kidneys. The first image data provision unit 12 provides first image data showing a region of interest of a patient acquired by the first imaging modality 2. Here, the first image data of the first imaging modality 2 are CT image data.

The processing unit 13 registers the cavity model to the first image data and adapts the cavity model based on the first image data. Thereby, an adapted cavity model is achieved. The processing unit 13 is connected to the model provision unit 11 and the first image data provision unit 12. The adapting of the cavity model based on the first image data is performed in a fully automatic fashion.

The processing unit 13 may further be configured to apply a model-based segmentation to the first image data, based on the adapted model. That is, features in the first image data corresponding to features represented in the adapted model, such as the lungs, may be segmented in the image data.

The processing unit 13 differs between bony and non-bony structures and masks a non-bony structure, in particular the ventral cavity, in the first image data based on the adapted cavity model. Thereby, masked first image data are achieved.

The second image data provision unit 14 provides second image data showing the region of interest of a patient acquired by the second imaging modality 3. Here, the second image data of the second imaging modality 3 are live X-ray image data.

The registration unit 15 registers the masked first image data and the second image data. Here, an overlay of CT image data on live X-ray data is achieved. The registration unit 15 is connected to the processing unit 13 and the second image data provision unit 14. The registration is here performed in an automatic fashion, but the user is given an option to initialize or post-correct the automatic segmentation.

The processing unit 13 may further estimate sub-volumes of certain bony landmarks in the first image data, in particular the spine, pelvis and/or ribs, based on the geometry of the adapted cavity model. That is, these sub-volumes may be derived from one or more parameters of the adapted model. Further, the processing unit 13 may be configured to selectively render these sub-volumes in the first image data. In other words, a rendering of these landmark structures may be enabled and disabled, preferably by means of a user interaction.

The processing unit 13 is further configured to mask tissue and/or a vasculature structure in the first image data based on the adapted cavity model. In particular, at least part of an interior of the ventral cavity, for example including contrast-enhanced vasculature, may be masked out. As a result, visibility of certain bony landmarks will be enhanced.

The imaging system 1 for registration of different imaging modalities further comprises a display unit 4 to visualize the registered image data and a landmark within the registered image data to allow an inspection of the registration. The landmark may be based on a bony structure.

The imaging system 1 for registration of different imaging modalities further comprises a selector 5 to select between the visualization of the enclosed volume or of a sub-volume. The sub-volume maybe e.g. a spine sub-volume and/or a rib cage sub-volume. By using the selector 5, the user can choose to visualize the volume as, e.g. a full volume, a spine and rib cage visualization and/or a spine only volume.

The imaging system 1 for registration of different imaging modalities further comprises an input device 6 configured to control the segmentation and/or an alignment of the registration. The segmentation and/or alignment of the registration may be based on the selected visualization of the enclosed volume or of a sub-volume. By using the input device 6, the user may align e.g. the CT and X-ray image data sets, using the selective CT visualization as a guideline.

The imaging system 1 for registration of different imaging modalities further comprises a bone booster 7 configured to boost a visualization of a bony landmark in the second image data, and in particular in 2D X-ray image data. That is, an image processing algorithm is applied to the 2D X-ray image data that enhances the visibility of the structures of interest, such as a contrast and/or an edge enhancement algorithm.

The display unit 4, the selector unit 5, the input device 6 and the bone booster 7 are connected to the registration unit 15.

Figure 2:
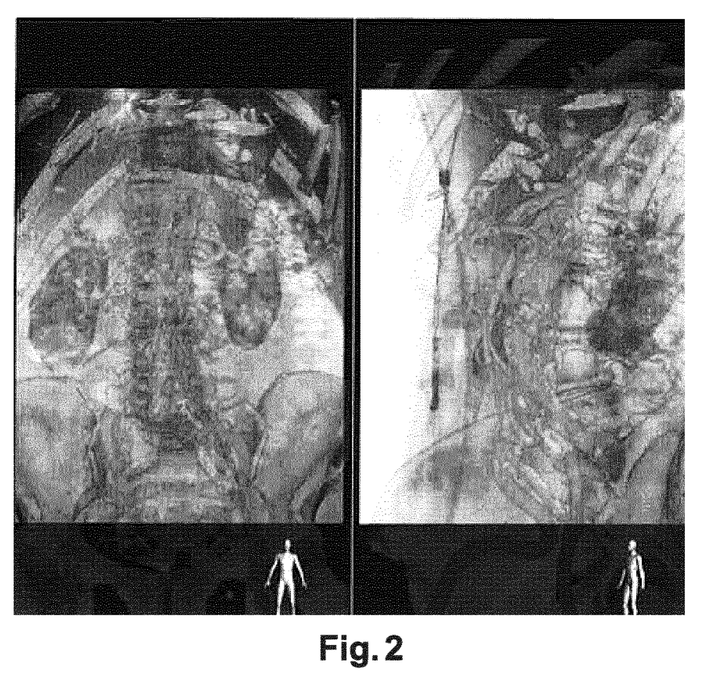
FIGS. 2 to 5 show schematically and exemplarily different overlays of CT and X-ray as first and second image data.
Figure 3:
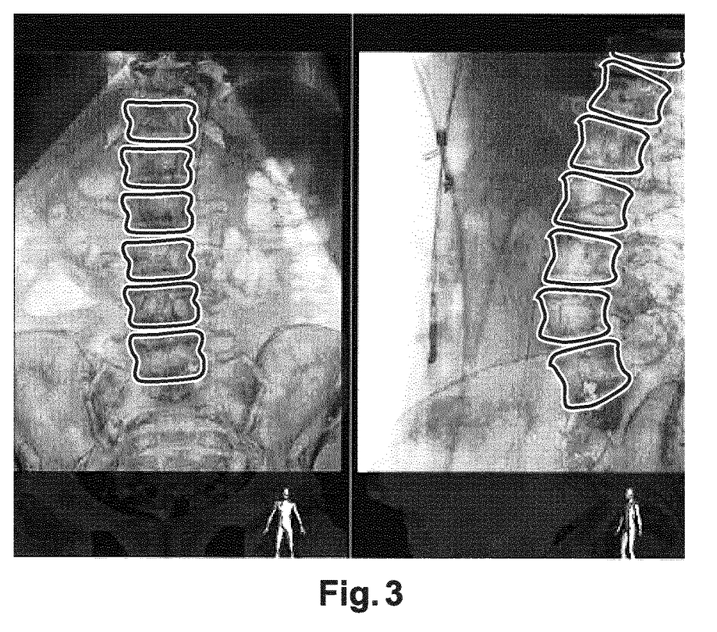
Figure 4:
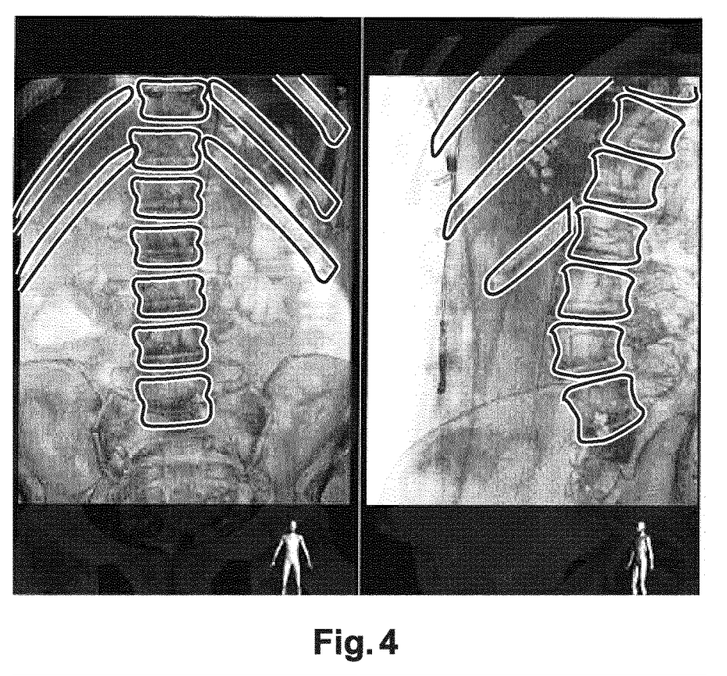
Figure 5:
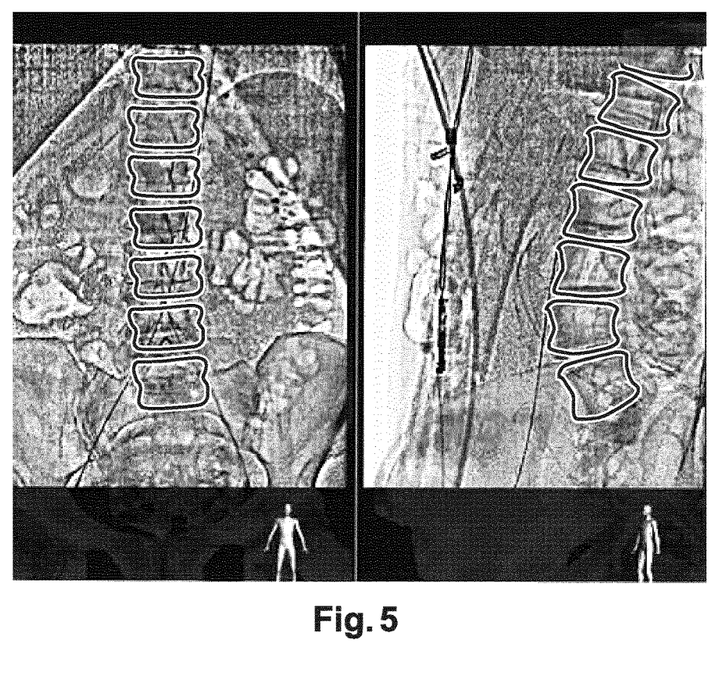

FIGS. 2 to 5 show schematically and exemplarily different overlays of CT and X-ray as first and second image data seen from AP (left) and with a 60° rotation angle (right). FIG. 2 corresponds to the prior art. It is difficult to see how well the spine and thorax in the volume are aligned with the X-ray data. FIGS. 3 to 5 show overlays of CT and X-ray according to the present invention.

FIG. 3 shows an X-ray with CT overlay of the spine only. It is now significantly easier to translate and align the spinal column (marked by border strips). FIG. 4 shows an X-ray with CT overlay of the spine and thoracic bones (both marked by border strips). While the ribs may partially occlude the view on the spine, they may help aligning the rotation of the volume. FIG. 5 shows a bone boosted X-ray with CT overlay of the spine only (marked by border strips). The combination of bone boosting the X-ray and selectively showing the bones in 3D makes registration less time consuming and significantly more accurate.

Figure 6:
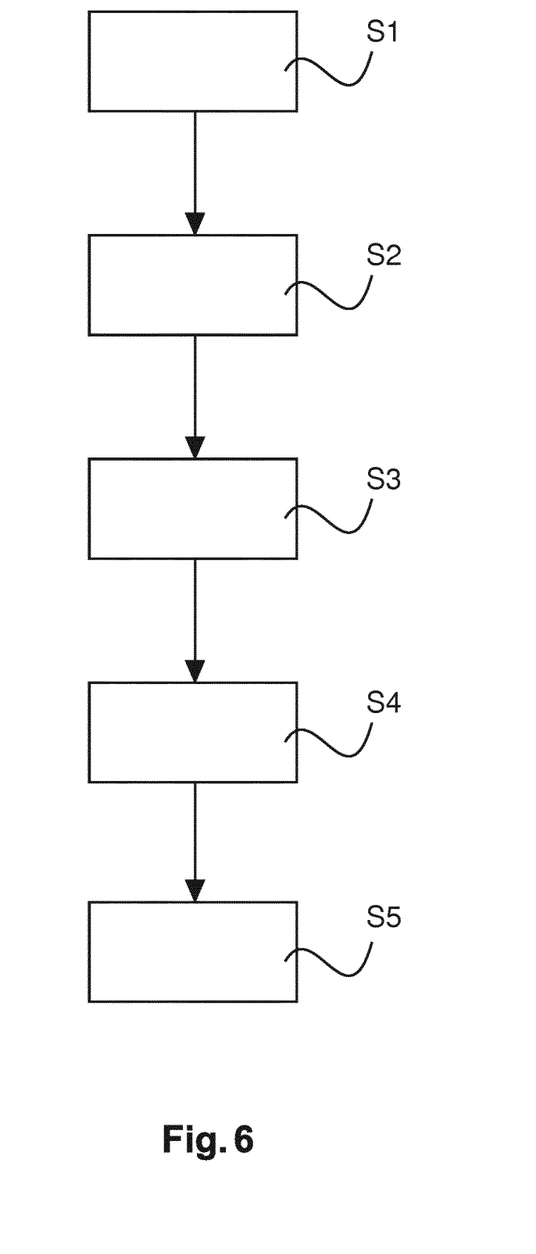
FIG. 6 shows basic steps of an example of a method for registration of different imaging modalities.

FIG. 6 shows a schematic overview of steps of a method for registration of different imaging modalities. The method comprises the following steps, not necessarily in this order:

In a first step S1, providing a cavity model of a visceral cavity.
In a second step S2, providing first image data.
In a third step S3, adapting the cavity model based on the first image data.
In a fourth step S4, masking non-bony structures in the first image data based on the adapted cavity model.
In a fifth step S5, registering the masked first image data and the second image data.

In another exemplary embodiment of the present invention, a computer program or a computer program element is provided that is characterized by being adapted to execute the method steps of the method according to one of the preceding embodiments, on an appropriate system.

The computer program element might therefore be stored on a computer unit, which might also be part of an embodiment of the present invention. This computing unit may be adapted to perform or induce a performing of the steps of the method described above. Moreover, it may be adapted to operate the components of the above described apparatus. The computing unit can be adapted to operate automatically and/or to execute the orders of a user. A computer program may be loaded into a working memory of a data processor. The data processor may thus be equipped to carry out the method of the invention.

This exemplary embodiment of the invention covers both, a computer program that right from the beginning uses the invention and a computer program that by means of an up-date turns an existing program into a program that uses the invention.

Further on, the computer program element might be able to provide all necessary steps to fulfil the procedure of an exemplary embodiment of the method as described above.

According to a further exemplary embodiment of the present invention, a computer readable medium, such as a CD-ROM, is presented wherein the computer readable medium has a computer program element stored on it, which computer program element is described by the preceding section.

A computer program may be stored and/or distributed on a suitable medium, such as an optical storage medium or a solid state medium supplied together with or as part of other hardware, but may also be distributed in other forms, such as via the internet or other wired or wireless telecommunication systems.

However, the computer program may also be presented over a network like the World Wide Web and can be downloaded into the working memory of a data processor from such a network. According to a further exemplary embodiment of the present invention, a medium for making a computer program element available for downloading is provided, which computer program element is arranged to perform a method according to one of the previously described embodiments of the invention.

It has to be noted that embodiments of the invention are described with reference to different subject matters. In particular, some embodiments are described with reference to method type claims whereas other embodiments are described with reference to the device type claims. However, a person skilled in the art will gather from the above and the following description that, unless otherwise notified, in addition to any combination of features belonging to one type of subject matter also any combination between features relating to different subject matters is considered to be disclosed with this application. However, all features can be combined providing synergetic effects that are more than the simple summation of the features.

While the invention has been illustrated and described in detail in the drawings and foregoing description, such illustration and description are to be considered illustrative or exemplary and not restrictive. The invention is not limited to the disclosed embodiments. Other variations to the disclosed embodiments can be understood and effected by those skilled in the art in practicing a claimed invention, from a study of the drawings, the disclosure, and the dependent claims.

In the claims, the word "comprising" does not exclude other elements or steps, and the indefinite article "a" or "an" does not exclude a plurality. A single processor or other unit may fulfil the functions of several items re-cited in the claims. The mere fact that certain measures are re-cited in mutually different dependent claims does not indicate that a combination of these measures cannot be used to advantage. Any reference signs in the claims should not be construed as limiting the scope.

The invention claimed is:

1. An imaging device for registration of different imaging modalities, comprising:
a model provision unit configured to provide a cavity model of a ventral cavity,
a first image data provision unit configured to provide first image data showing a region of interest of a patient by a first modality, the region of interest including the ventral cavity, the first image data of the first modality being CT or MR image data,
a processing unit configured i) to register the cavity model to the first image data, ii) to adapt the cavity model based on the first image data and iii) to mask at least part of the ventral cavity in the first image data based on the adapted cavity model in order to produce masked first image data in which voxels are masked so that vascular features inside the mask are removed, a second image data provision unit configured to provide second image data showing at least part of the region of interest of a patient by a second modality, the second image data of the second modality being live X-ray image data, a registration unit configured to register the masked first image data in which the voxels are masked so that the contents inside the mask are removed and the second image data.

2. Imaging device according to claim 1, wherein the ventral cavity in the first image data is segmented based on the adapted cavity model.

3. Imaging device according to claim 2, wherein the ventral cavity model includes at least one organ of a chest and/or an abdomen.

4. Imaging device according to claim 1, wherein the at least part of the ventral cavity being masked in the first image data includes contrast enhanced vasculature.

5. Imaging device according to claim 1, wherein the processing unit is configured to estimate a sub-volume of at least one bony landmark in the first image data based on at least one parameter of the adapted cavity model.

6. Imaging device according to claim 5, wherein the processing unit is configured to selectively render the sub-volume in the first image data.

7. An imaging system for registration of different imaging modalities, comprising:
a first imaging modality comprising a computed tomography (CT) device or a magnetic resonance (MR) imaging device,
a second imaging modality comprising an X-ray device, and
an imaging device according to claim 1,
wherein the first and second imaging modalities acquire the first and second image data to be provided by the first and second image data provision units.

8. Imaging system according to claim 7, further comprising a display unit configured to visualize the registered image data and a bony landmark within the registered image data.

9. Imaging system according to claim 7, further comprising a selector configured to selectively enable or disable a visualization of the sub-volume.

10. Imaging system according to claim 8, further comprising a bone booster configured to boost a visualization of the bony landmark in the second image data.

11. A non-transitory computer readable medium comprising instructions executable by a computer to perform a method for registration of different imaging modalities, the method comprising:
estimating a sub-volume of at least one bony landmark in CT or MR image data of a region of interest of a patient including a ventral cavity based on at least one parameter of a cavity model of the ventral cavity;
registering the cavity model to the CT or MR image data;
adapting the cavity model based on the CT or MR image data and the estimated sub-volume of the at least one bony landmark,
masking the ventral cavity in the CT or MR image data based on the adapted cavity model to produce masked CT or MR image data in which voxels are masked so that contents inside the mask are removed,
providing two dimensional (2D) X-ray image data showing at least part of the region of interest of the patient by a second modality and
registering the masked CT or MR image data in which the voxels are masked so that contents inside the mask are removed and the 2D X-ray image data.

12. An imaging device for registration of different imaging modalities, the imaging device comprising at least one computer programmed to:
register a cavity model of a ventral cavity to first image data, the first image data showing a region of interest of a patient by a first modality, the region of interest including at least one bony structure disposed in the ventral cavity, the first image data of the first modality being CT or MR image data;
adapt the cavity model based on the first image data;
mask at least part of the ventral cavity in the first image data based on the adapted cavity model;
provide second image data showing at least part of the region of interest of a patient by a second modality, the second image data of the second modality being two-dimensional (2D) X-ray image data; and
register the masked first image data and the second image data.

13. The imaging device according to claim 12, wherein the ventral cavity in the first image data is segmented based on the adapted cavity model.

14. The imaging device according to claim 13, wherein the ventral cavity model includes at least one organ of a chest and/or an abdomen.

15. The imaging device according to claim 12, wherein the at least part of the ventral cavity being masked in the first image data includes contrast enhanced vasculature.

16. The imaging device according to claim 12, wherein the at least one computer is programmed to:
estimate a sub-volume of the at least one bony landmark in the first image data based on at least one parameter of the adapted cavity model; and
selectively render the sub-volume in the first image data.

17. An imaging system for registration of different imaging modalities, comprising:
a first imaging modality comprising a computed tomography (CT) device or a magnetic resonance (MR) imaging device,
a second imaging modality comprising an X-ray imaging device, and
an imaging device according to claim 15,
wherein the first and second imaging modalities acquire the first and second image data to be provided by the first and second image data provision units.

18. The imaging system according to claim 17, further comprising a display device configured to visualize the registered image data and a bony landmark within the registered image data.

19. The imaging system according to claim 18, further comprising a selector configured to selectively enable or disable a visualization of the sub-volume.

20. The imaging system according to claim 18, further comprising a bone booster configured to boost a visualization of the bony landmark in the second image data.

* * * * *